US006183742B1

(12) United States Patent
Kiczka

(10) Patent No.: US 6,183,742 B1
(45) Date of Patent: Feb. 6, 2001

(54) APPLICATIONS OF LYSOZYME DIMER

(75) Inventor: Witold Kiczka, Princeton, NJ (US)

(73) Assignee: Nika Health Products, Limited, Vaduz (LI)

( * ) Notice: Under 35 U.S.C. 154(b), the term of this patent shall be extended for 0 days.

(21) Appl. No.: 09/348,822

(22) Filed: Jul. 8, 1999

Related U.S. Application Data

(62) Continuation of application No. 08/815,009, filed on Mar. 14, 1997, now abandoned, which is a continuation-in-part of application No. PCT/EP96/00135, filed on Jan. 13, 1996, and a continuation-in-part of application No. 08/351,375, filed as application No. PCT/EP93/01841 on Jul. 13, 1993, now abandoned.

(30) Foreign Application Priority Data

Jan. 13, 1995 (EP) .................................. 95100446
Jul. 7, 1995 (EP) .................................. 95110638
Jul. 13, 1992 (PL) ...................................... 295273

(51) Int. Cl.$^7$ .................................................. A61K 38/47
(52) U.S. Cl. .......................................................... 424/94.61
(58) Field of Search ................................ 424/94.1, 94.61

(56) References Cited

U.S. PATENT DOCUMENTS

| 5,118,500 | 6/1992 | Hänel et al. . |
| 5,200,182 | 4/1993 | Kiczka . |
| 5,244,902 | 9/1993 | Sharpe et al. . |
| 5,260,182 | 11/1993 | Nagaoka et al. . |
| 5,314,816 | 5/1994 | Uermann et al. . |
| 5,317,019 | 5/1994 | Bender et al. . |
| 5,420,154 | 5/1995 | Christensen, IV et al. . |
| 5,466,449 | 11/1995 | Kiczka . |

FOREIGN PATENT DOCUMENTS

| 0181634 | 5/1986 | (EP) . |
| 0238851 | 9/1987 | (EP) . |
| 4020 M | 4/1966 | (FR) . |
| 2215201 | 8/1974 | (FR) . |
| 55-33408 | 3/1980 | (JP) . |
| 55-33409 | 3/1980 | (JP) . |
| 55-43040 | 3/1980 | (JP) . |
| 4234804 * | 8/1992 | (JP) . |
| WO 89/11294 | 11/1989 | (WO) . |
| WO 91/10731 | 7/1991 | (WO) . |
| WO 94/01127 | 1/1994 | (WO) . |

OTHER PUBLICATIONS

Database JPO and Japio on Dialog, No. 03869704, JP 4234804 A, Aug. 1992.*
Henry, J.B., "Imunosuppressive", pp. 371–372, in Clinical Diagnosis and Management by Laboratory Methods, 18th ed., W.B. Saunders Company, Philadelphia, 1991.*
Kiczka, W., proceedings 18th World Buiatrics Congress, Bologna, Italy, vol. 1, pp. 897–900. Trenti, R., ed., Aug. 1994.*
Switala et al., Polish Journal of Pharmacology, 47 (Suppl), p. 117, 1995.*
Switala et al., Polish Journal of Pharmacology, 47 (Suppl), p. 118, 1995.*
Valic et al., Lijec Vjesn (Yugoslavia), 112(1–2):1–6, Aug. 1992.*
Katsutoshi Takada et al., "Binding of Lysozyme to Lipopolysaccharide Suppresses Tumor Necrosis Factor Production In Vivo," *Infection and Immunity*, vol. 62, No. 4, pp. 1171–1175, 1994.
Ana J. Coito et al., "Anti–TNF–α Treatment Down–Regulates the Expression of Fibronectin and Decreases Cellular Infiltration of Cardiac Allografts in Rats[1]," *Journal of Immunology*, vol. 154, pp. 2949–2958, 1995.
Jacques Bartholeyns et al. "In Vitro and In Vivo Antitumor Effect of Dimerized Ribounclease A*," *European Journal of Cancer*, vol. 15, pp. 85–91, 1979.
J. Bartholeyns, et al., Archives Internationales de Physiologie et de Biochimie, vol. 87(1), pp. 155–156 (Feb. 1979).
Annapuma Vyakamam et al., "Tumour Necrosis Factors (α, β) Induced by HIV–1 in Peripheral Blood Mononuclear Cells Potentiate Virus Replication," *AIDS*, vol. 4, No. 1, pp. 21–27, 1990.
Katherine F. Bayston et al., "Bacterial Endotoxin and Current Concepts in the Diagnosis and Treatment of Endotoxaemia," *J. Med. Microbiol.*, vol. 31, pp. 73–83, 1990.
Dennis L. Stevens et al., "Gram–positive Shock," *Current Opinion in Infectious Diseases*, vol. 5, pp. 355–363, 1992.
Frank E. Berkowitz, "Bacterial Toxins in the Pathogenesis of Infections," *Current Opinion in Infectious Diseases*, vol. 4, pp. 332–337, 1991.
Philip A. Mackowiak, "Mechanism of Fever," *Current Opinion in Infectious Diseases*, vol. 5, pp. 348–354, 1992.
Toshifumi Matsuyama et al., "Cytokines and HIV Infection: Is AIDS a Tumor Necrosis Factor Disease?," *AIDS*, vol. 5, pp. 1405–1417, 1991.
Masahiko Ito et al., "Tumor Necrosis Factor Antagonizes Inhibitory Effect of Azidothymidine on Human Immunodeficiency Virus (HIV) Replication In Vitro," *Biochemical Research Communications*, vol. 166, No. 3, pp. 1095–11101, Feb. 14, 1990.
Cakala et al., Proceedings 18$^{th}$ World Buiatrics Congress of the Italian Association of Buiatrics, Bologna, Italy, Aug. 29–Sep. 2, 1994, vol. 1, pp. 607–610.

* cited by examiner

Primary Examiner—Donna C. Wortman
Assistant Examiner—Brenda G. Brumback
(74) Attorney, Agent, or Firm—Oliff & Berridge, PLC

(57) ABSTRACT

A method for treating or preventing a disease includes administering a pharmaceutical composition containing a lysozyme dimer to a human or animal recipient in an amount effective for non-specific stimulation of the immune system or the regenerative mechanisms of the human or animal body, and wherein the disease is selected from the group consisting of leukemia, hair growth disorder, a fish disease and a bee disease. The method can be used for treating or preventing such diseases as leukemia, hair growth disorder, a fish disease and a bee disease. In addition, the method can be used for immunomodulating a humoral response in a human or animal subject to immunosuppression, such as for positively affecting the primary humoral response of mammals immunized with an antigen after immunosuppression.

11 Claims, 4 Drawing Sheets

Fig. 3   Effects of Lydium-KLP(μ20g/kg) depending on the number of injections and timing in relation to cyclophosphamide (CY) injected 6 days prior to SRBC injection

| GROUPS | n | Day 4 after SRBC ||||| Day 7 after SRBC |||||
|---|---|---|---|---|---|---|---|---|---|---|---|
| | | PFC N/1x10⁶ | 19S+7S log₂ titre | 7S log₂ titre | EAC % | E % | PFC N/1x10⁶ | 19S+7S log₂ time | 7S log₂ time | EAC % | E % |
| CONTROL | 8 | 1282 ±167 | 7.8 ±0.6 | 2.6 ±0.6 | 52.2 ±6.9 | 14.7 ±2.4 | 521 ±64 | 9.0 ±0.6 | 8.3 ±0.7 | 48.0 ±6.8 | 15.5 ±3.3 |
| CY (200mg/kg) | 11 | 239* ±75 | 4.2* ±1.1 | 0 | 29.8* ±5.9 | 16.4 ±3.2 | 209* ±65 | 6.4* ±0.9 | 4.6* ±1.3 | 34.5* ±8.6 | 15.6 ±3.1 |
| Lydium-KLP - single dose 2 days prior to CY | 10 | 311** ±72 | 4.8* ±1.0 | 0 | 29.4* ±5.7 | 13.9 ±3.5 | 341** ±96 | 7.3* ±0.4 | 5.0* ±0.7 | 29.5* ±6.0 | 13.9 ±2.6 |
| Lydium-KLP - single dose 4 days prior to CY | 9 | 362** ±70 | 4.2* ±0.7 | 0 | 32.9* ±8.1 | 13.6 ±2.9 | 370*♦ ±180 | 7.1* ±1.7 | 5.4* ±0.9 | 28.5* ±6.9 | 16.8 ±4.1 |
| Lydium-KLP - single dose 6 days prior to CY | 11 | 347** ±105 | 4.5* ±1.1 | 0.6* ±0.9 | 36.1* ±5.8 | 13.9 ±2.1 | 376*♦ ±122 | 6.9* ±0.8 | 5.1* ±1.3 | 26.6*♦♦ ±3.4 | 17.8 ±2.9 |
| Lydium-KLP - two doses 2 and 6 days prior to CY | 10 | 378** ±113 | 5.3*♦ ±0.5 | 0 | 42.0*♦ ±3.7 | 15.3 ±3.7 | 405*♦ ±86 | 8.1♦ ±0.9 | 6.6*♦ ±0.7 | 28.9* ±4.5 | 16.8 ±3.9 |
| Lydium-KLP - three doses 2, 4 and 6 days prior to CY | 10 | 549*♦ ±183 | 6.8*♦ ±1.1 | 1.3* ±1.4 | 44.4*♦ ±7.0 | 18.4 ±4.9 | 444♦ ±88 | 8.9♦ ±0.8 | 8.3 ±1.3 | 30.8* ±4.7 | 14.9 ±4.7 |

\* p<0.05 as compared to control group
♦ p<0.05 as compared to cyclophosphamide group

APPLICATIONS OF LYSOZYME DIMER

This application is a Continuing Application of U.S. application Ser. No. 08/815,009, filed Mar. 14, 1997, now abandoned, which in turn is a Continuation-In-Part of International Application No. PCT/EP96/00135, filed Jan. 13, 1996, and U.S. application Ser. No. 08/351,375, filed Feb. 13, 1995, now abandoned, which is the U.S. National Stage application of International Application No. PCT/EP93/01841, filed Jul. 13, 1993. The entire disclosure of the prior application is hereby incorporated by reference herein in its entirety.

BACKGROUND OF THE INVENTION

The present invention relates to new applications of lysozyme dimer and to compositions containing such dimer. The new applications are based on a common principle of non-specific stimulation of the immune system and are particularly useful for the prevention and/or treatment of symptoms or diseases in connection with an impaired function of the natural defensive and regenerative systems in the human and animal body. In particular, the present invention relates to uses of the lysozyme dimer to restore a suppressed immune system in humans and animals.

In the late 1980s, it was discovered that the dimerized forms of certain enzymes, while substantially retaining the beneficial properties of the corresponding monomers, turned to be by far less toxic than the monomers themselves and in some instances did not even display negative side effects at all when used in therapeutic doses. Antiviral and antibacterial compositions comprising as the active ingredient lysozyme dimer or other dimerized enzymes have been described in WO 89/11294. It is reported therein that lysozyme dimer is capable of inhibiting proliferation of a number of bacterial strains cultivated on samples taken from patients, when applied in concentrations of 1.25–20 mg/ml of the culture. It is also reported that the dimer is effective in treating canine parvovirus (CPV) infections when administered orally twice a day at a dose of 1–2 mg/kg of body weight. Later on, further attractive features of lysozyme dimers were found and additional therapeutical applications of the drug were developed, especially for the treatment of bacterial and viral infections as disclosed, for instance, in WO 94/01127.

In WO 94/01127, a model theory is presented that can help to understand the different effects observed with the lysozyme dimer. Although the entire mode of action of the lysozyme dimer is not yet fully understood, it appears that there is additional curative capability that cannot be explained by the bacteriolytic activity of the corresponding monomer. The inventors observed certain immunostimulative effects of the dimerized lysozyme, particularly concerning the modulation of cytokine levels. Moreover, from their experiments, they concluded that lysozyme dimer seems to prevent the penetration of bacterial cells by viruses, presumably by blocking certain regions of the outer cell surface and probably comprising virus receptor proteins.

The prior art discloses further results obtained in vitro with lysozyme dimer. Particularly, Bartholeyns and Zenebergh (Europ. J. Cancer, Vol.15, 1979, 85–91) tested dimerized lysozyme for cytostatic activities against liver cancer cells (HCT) in vitro. They observed a 73%±15% inhibition of cancer cell multiplication in the cell culture (ibid., p.89, Table 2).

Surprisingly, except for WO 94/01127, no in vivo experiments with lysozyme dimer are reported so far. It is very strange and astonishing, and up to now waits for explanation, why neither Bartholeyns and Zenebergh nor any other researcher resumed this subject to promote further development of a promising discovery to combat cancer. A comparative showing (FIG. 1) of the purity of lysozyme dimer produced according to the method of Sorrentino et al., Eur. J. Biochem. 124, 183–189 (1982) and of the lysozyme dimer preferably used in the present invention revealed at least one possible reason: high concentrations of by-products such as lysozyme monomer, trimer and tetramer are found in the preparation produced according to Sorrentino et al., whereas the product preferably used in the present invention is highly purified, i.e., contains the desired lysozyme dimer in amounts of up to 90% or more by weight of the total lysozyme fraction of the preparation. A process for the manufacture of such highly purified lysozyme dimer has been described in WO 91/10731, the entire disclosure of which is incorporated herein by reference. This strongly supports the assumption that the purity of the prior art lysozyme dimer was simply not good enough for in vivo experiments and applications because it was known in the art already over 15 years ago that the monomeric form of lysozyme, despite its beneficial antibacterial activity, is rather toxic and can cause inflammations and severe allergies and even toxic shock symptoms.

In light of such circumstances it appears more understandable why no competent researcher including Bartholeyns and Zenebergh—although recommending lysozyme dimer as a promising candidate for further investigations—has carried out further experiments during the past ten to fifteen years to develop lysozyme dimer applications in vivo.

In spite of such lack of research activities of the scientific world possibly due to a prejudice of the art against the use of lysozyme dimer in vivo, the present inventors carried out further research and developmental work to improve the method of production and purification of the dimerized lysozyme and to find in vivo human and animal applications for the product, which led, for instance, to the antiviral and antibacterial and TNF level modulating applications disclosed in WO 94/01127, and the entire disclosure of which is incorporated herein by reference.

Use of immunostimulants, adjuvants and vaccines offers a wide range of attractive methods for inducing and building up protection against diseases. In this respect, "immunostimulants" refer to compounds that only stimulate non-specific defense mechanisms and protect against diseases. "Immunomodulators" refer to compounds that regulate (or modulate) the defense mechanisms after suppression (or decrease of immunity) of those mechanisms. Such suppression can arise from or be induced by many sources including pollutants, chemotherapeutics, stress, food, temperature changes, and the like. Immunomodulators stabilize the defense mechanisms after the influence of pathogens, and increase cellular and humoral immunity. Some immunomodulators are also able to depress and/or normalize hyperactive defense mechanisms including modulation of cytokine levels. Many immunostimulants are also classified as immunomodulators.

In the field of vaccine medicine, it is common that the patient exhibits only a small positive reaction to the vaccine, which thus provides only minimal protection. Many studies have shown or theorized that the effect of a vaccine is determined by the level of cell-mediated immunity and activity of cells for the production of specific antibodies. It has been known that many factors, such as products, drugs, particularly antibiotics, pollutants and stress, decrease the level of defense mechanisms and cell-mediated immunity.

Thus if the humoral response mechanisms are suppressed, effectiveness of a subsequently administered vaccine can be reduced or even eliminated.

In an effort to overcome these problems, adjuvants have typically been used in combination with vaccine preparations. Adjuvants are substances used to enhance the specific immune response. Adjuvants are generally mixed and injected with antigen preparations, acting to elevate the specific immune activity. That is, the adjuvants generally are used to increase the level of antibody secreting cells circulating antibody titres. Adjuvants thus generally potentiate the specific immune response and stimulate production of specific antibodies.

Complete Freund's adjuvant is the classic adjuvant, inducing an inflammatory response at the injection site. Freund's adjuvants, combining paraffin oil and killed tubercle bacilli, were among the first immunostimulants used in humans and animals that were mixed with immunogens. Lanolin, paraffin or other various light oils were also used in conjunction with bacterin or vaccines. Unfortunately, these oil adjuvants can not be used as immunostimulants in routine immunization because, by their very nature, adverse inflammatory reactions often occur at the injection site. One example of a suitable adjuvant, approved by the U.S. Food and Drug Administration for use in humans in the United States, is alum or aluminum-phosphate precipitate, as used with diphtheria toxin.

Moreover, based on their knowledge of low toxicity of dimerized lysozyme compared to the monomer and on the availability of a new, highly purified lysozyme dimer preparation, the present inventors attempted and started anti-cancer trials with lysozyme dimer preparations in vivo, although the prior art did not suggest its use to treat diseases other than bacterial or viral infections. It is an advantage of the present invention to provide for the use of a highly purified lysozyme dimer for the manufacture of a pharmaceutical composition to supplement or replace the extremely toxic anti-cancer drugs usually applied in conventional chemotherapy.

Further investigative work by the present inventors has also revealed additional advantageous uses of the lysozyme dimer. Recent studies on immunomodulating properties of the lysozyme dimers have shown that it potentiates humoral response in mammals. In particular, the lysozyme dimer has been found to have the unexpected advantage of being capable of positively affecting the primary humoral response of mammals immunized with an antigen after immunosuppression. Such immunomodulating properties of the lysozyme dimer were not taught or suggested by the prior art.

Accordingly, in this respect, the present invention provides a method for increasing the cellular and humoral immunity response mechanisms after their suppression by some means such as toxic effects of antibiotics or chemicals. This is a completely new idea in the area of immunology. The concept of the present invention is to modulate non-specific cellular and humoral defense mechanisms, which form the first line of protection in immunology.

In particular, the present invention is directed to a method for treating or preventing a disease, comprising administering an effective amount of a pharmaceutical composition comprising a lysozyme dimer, wherein said lysozyme dimer contains about 10% by weight or less of unintended byproducts and is essentially free from a monomeric form of lysozyme, and wherein the disease is selected from the group consisting of cancer, hair growth disorder, a fish disease and a bee disease.

The present invention is also directed to a method for immunomodulating a humoral response in a human or animal subject to immunosuppression, comprising administering an effective amount of a pharmaceutical composition comprising a lysozyme dimer, wherein said lysozyme dimer contains about 10% by weight or less of unintended byproducts and is essentially free from a monomeric form of lysozyme.

These and other advantages are provided by the present invention.

BRIEF DESCRIPTION OF THE DRAWINGS

FIG. 3 shows dose-dependent effect of lysozyme dimer administered prior to cyclophosphamide on humoral response in SRBC-immunized mice.

DETAILED DESCRIPTION OF PREFERRED EMBODIMENTS

Figure 1:
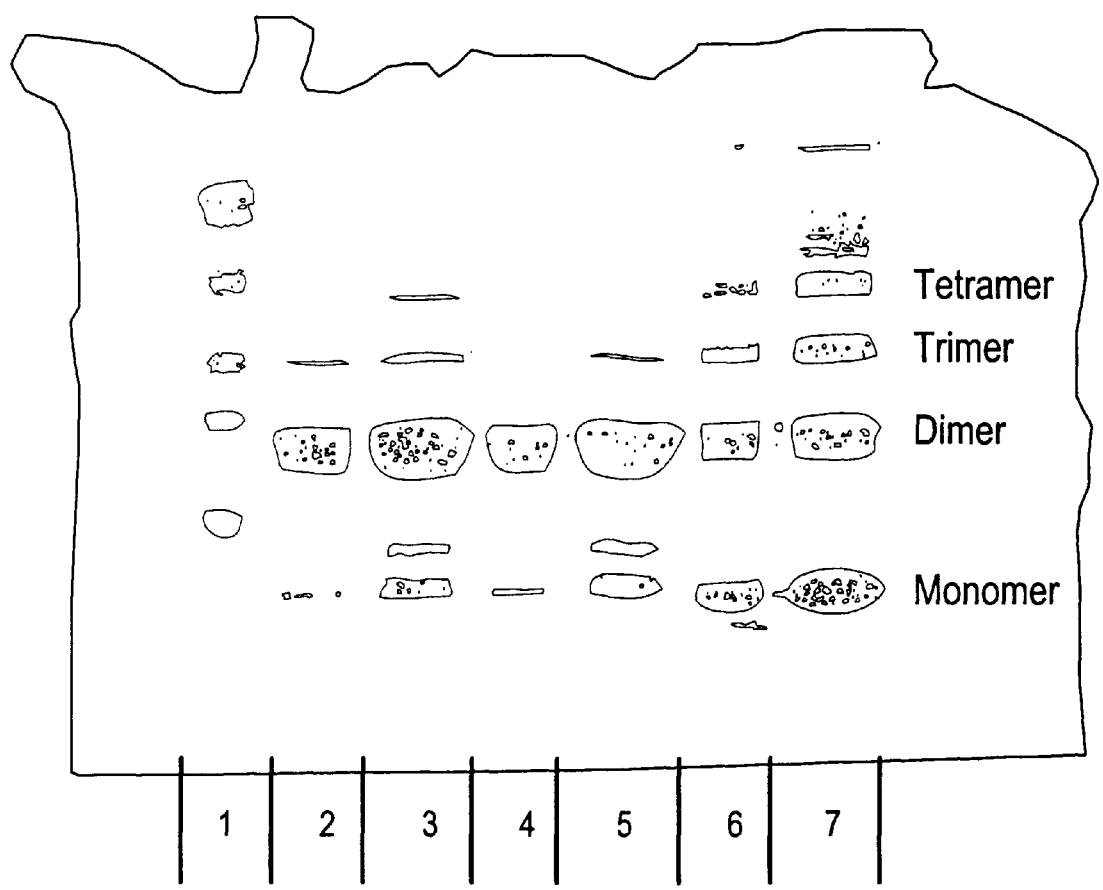
FIG. 1 displays a comparative showing of the purity of lysozyme dimer preparations manufactured according to two different prior art techniques.

The highly purified lysozyme dimer referred to in the present invention can be used for the manufacture of pharmaceutical compositions directly applicable for the treatment of animals and humans due to its low amount of toxic monomer.

As indicated above, such purified lysozyme dimer contains about 10% wt. or less of unintended by-products, and can be obtained via dimerization of lysozyme monomers of any origin, e.g. of lysozyme monomers derived from humans, animals, eggs, plants, microorganisms, the monomers being either naturally isolated in native form or manufactured via chemical or genetic engineering methods to yield lysozyme monomers of the same or essentially the same chemical and biological nature as the naturally occurring ones.

In tests on in vitro cell cultures and in vivo test models, preferably mice and rat test models, the inventors of the present invention could successfully demonstrate that the applied lysozyme dimer compositions display remarkable potency in the inhibition or even total prevention of cell proliferation of leukemic cells in vivo, particularly in the case of virus induced lymphatic leukemia.

It is an object of the present invention to provide for a pharmaceutical composition and a method to prevent and/or treat leukemia, particularly lymphatic leukemia induced by a virus such as a retrovirus including HTLV-I (adult T-cell leukemia virus) in animals and humans.

Another beneficial application of the highly purified lysozyme dimer was surprisingly discovered in clinical trials when lysozyme dimer compositions were administered to patients with more or less infected postoperative wounds, e.g. after amputation of a lower extremity. It turned out that the local application of the dimer not only successfully defeated the wound infection but also stimulated hair growth and hair renewal within the treated area. This surprising discovery led to further investigations and finally to the manufacture of pharmaceutical compositions applicable in cases of hair growth disorders, particularly hair growth disorders based on immunological malfunctions or dysfunctions such as, e.g., in case of alopecia areata.

Such compositions can at least partly fulfill the criteria of a long desired composition acting as a hair growth stimulant. The underlying principle of this completely unexpected effect is believed to comprise amongst others the stimulation and improvement of immune defense mechanisms, improvement of the blood circulation in the superficial tissue layers and the skin, general non-specific improvement of immunological functions and, probably, some more still unidentified effects.

Another surprising and commercially very interesting application for a pharmaceutical composition containing lysozyme dimer has been found in fish farming and bee-keeping when in a screening experiment conventional antibiotics have been replaced with different non-specific immunostimulants including also the lysozyme dimer.

The use of immunostimulants in fish culture for the prevention and/or therapy of fish diseases is a promising new development (Siwicki and Anderson 1990; Siwicki et al. 1994). At present, substances for treating fish diseases include antibiotics, drugs and chemicals used for sterilizing fishholding ponds (Stoskopf, 1993). While each therapy is at least partially effective in the treatment of a particular disease, problems arise with the accumulation of these substances in the environment and in the meat of the fish as well as with the emergence of pathogenic strains of microorganisms resistant against various antibiotics.

In the case of bee-keeping, it is a widespread practice to kill colonies of bees if there is evidence that the bees are affected by microbial, e.g., bacterial and/or viral, infections. Such practice avoids spreading the infections among other colonies and thereby minimizes the losses. There is therefore a need to provide an alternative and reliable method for the prophylactic and/or therapeutic treatment of bees, for example of honey-bees, that combines both the advantage of an antibiotic additionally strengthening the immune system of bees and an antibiotic that will not result in the development of antibiotic-resistant microbial strains. The present invention provides for a method to meet such need. Moreover, even if lysozyme dimer was present in the final honey product in detectable concentrations, this would likely be regarded as an improvement of quality rather than as a change to the worse, due to the benefit of the non-specific immunomostimulative effect of lysozyme dimer.

In general, immunostimulants comprise a group of biological and synthetic compounds that enhance the non-specific cellular and humoral defense mechanisms in animals and humans. Immunostimulants such as beta-glucan, chitosan, levamisole, trace mineral and mineral combinations, and various products derived from many plant and animal sources are effective in preventing diseases. Several types of beta-glucans seem to be especially promising for the stimulation of the cellular and humoral non-specific immune response of fish.

The non-specific defense mechanisms which include phagocytosis and the production of oxidative radicals by polymorphonuclear (PMN) and mononuclear (MN) cells are quickly activated by the immunostimulants and are rapidly prepared to protect the fish against pathogenic microorganisms such as, for example, viruses, bacteria, mycoplasms and funghi, and/or against parasites or other pathogenic agents. Thus, these mechanisms are superior to the specific immune response that requires a longer period of time for the development of a specifically adapted immune response including antibody build-up and specific cellular activation.

The very encouraging results obtained in the first in vivo trials, indicating significant improvement of immunological defense mechanisms, have led to launching a detailed research program on the effect of lysozyme dimer on the specific and non-specific cellular and humoral defense mechanisms of fish, particularly of trout and salmon, and of honey-bees.

Therefore, it is an object of the present invention to provide for novel applications of lysozyme dimer comprising its use for the manufacture of a pharmaceutical composition for the stimulation of a non-specific cellular and humoral immune response in fish and honey-bees.

It is another object of the present invention to provide for a method of using pharmaceutical compositions containing said lysozyme dimer to induce a non-specific stimulation of the immune system by a single or repeated application of the composition, for the prevention and/or therapy of naturally occurring diseases of fish and bees.

In vivo experiments have shown that in some cases, e.g., where the fish are readily impaired by certain chemicals or undesired bioactive substances such as by-products of pharmaceuticals administered to them, it might be preferable to treat the fish with the highly purified lysozyme dimer reported in WO 91/10731, which contains about 10% by weight or less of unintended by-products and which is essentially free from the monomeric form of lysozyme. In order to reduce breeding costs in fish farming and/or in bee-keeping it might, however, also be acceptable to administer a lysozyme dimer preparation of lower purity as long as it is applied at a dose that does not cause adverse effects due to the presence of toxic by-products, especially Of lysozyme monomer.

The lysozyme dimer referred to in the present invention can also advantageously, and quite unexpectedly, be used in methods for affecting the primary humoral response of animals immunized with an antigen after immunosuppression. The lysozyme dimer can be applied directly, or preferably can be applied in the form of a pharmaceutical composition as will be described below.

In the present invention, the lysozyme dimer can be administered to the patient either prior to, concurrent with, or subsequent to immunosuppression by pharmacological, environmental, or other agents. However, for maximum effectiveness, the lysozyme is preferably administered prior to the immunosuppression. On the contrary, administration of the lysozyme dimer after immunosuppression provides the least immunomodulation effects. In addition, the lysozyme dimer can be administered in one dose, or in several doses over a set treatment period. Preferably, the lysozyme dimer is administered in a series of multiple doses, for example three, over an established treatment period of, for example, 12 to 48 hours between doses. However, it will be understood by those skilled in the art, and based on the present disclosure, the dosages and treatment periods will vary depending on particulars of the specific patient and treatment objectives.

For use in the immunomodulation methods of the present invention, each dose of lysozyme dimer preferably contains from about 1.0 to about 100, preferably about 1 to about 50, and more preferably from about 2 to about 20, $\mu$g/kg total body weight.

The exact mechanism of immunomodulation by the lysozyme dimer is still largely unknown and the subject of much experimentation and research. However, although not being limited to this specific explanation, it is believed that lysozyme dimer effects the restoration of T-helper lymphocytes, which increases antibody production. It is further believed that the lysozyme dimer provides the immunomodulating effects by activation of interleukin-6 (IL-6) and interleukin-2 (IL-2), reduced heterogeneity of splenic natural suppressor (NS) cells. It is also believed that the lysozyme dimer increases the production of alpha-interferon (alpha-IFN) and modulates the synthesis and release of tumor necrosis factor (alpha-TNF). Furthermore, IL-6 is considered to be responsible for ultimate differentiation in B lymphocytes (toward the cells able to produce immunoglobulins) and stimulation of T lymphocytes by inducing the receptor cells for IL-2 and enhanced IL-2 production. Administration of lysozyme dimer according to the methods of the present invention also effectively protects the primary humoral response, and increases the number of plaque forming cells (PFCs) and the level of anti-antigen haemagglutinins.

Furthermore, it is believed that administration of the lysozyme dimer according to the present invention can be used to retard degradation of the immune system. For example, the method of the present invention can be successively repeated to prevent degradation of the immune system, for example by alkylating cytostatic agents.

The lysozyme dimer referred to herein can either directly be applied to the patients in need thereof or can be used for the manufacture of pharmaceutical compositions to be applied in usual galenic forms. Gels, ointments, or liquid compositions comprise the lysozyme dimer preferably in a concentration of about 0.01–10 mg/ml and frequently in a concentration of about 0.1–1.0 mg/ml. They are usually prepared as sterile and apyrogenic compositions and optionally further comprise at least one physiologically acceptable solvent and/or carrier and/or at least one suitable preservative.

The pharmaceutical compositions containing lysozyme dimer are useful and intended primarily for topical and/or parenteral application comprising local injection, e.g., in the vicinity of a solid tumor, or external applications on the surface of the body including subcutaneous injection. Intravenous injections may replace or additionally support topical applications in the course of a therapy. It has, however, also proven very efficient to administer lysozyme dimer compositions to mucosal membranes, preferably via inhalation (nasal, mouth, pharyngeal mucosa) of liquid compositions or topical application (e.g. vaginal, cervical mucosa) of liquid or creamy compositions or tampons impregnated with lysozyme dimer material.

In some cases it is preferred to apply the lysozyme dimer orally, preferably in usual galenic forms such as for instance tablets, capsules or dragees or in the form of pellets, granules, flocs or as a powder. These solid compositions frequently contain the active drug in an amount of about 0.01–10 mg, preferably about 0.01–1.0 mg per g of the total composition. It is also preferred that they further comprise at least one suitable carrier and/or preservative and/or other usual additives such as for instance a flavor or a colorant. In case of treating fish, solid compositions may be added to the nutrients. Alternatively or additionally, the lysozyme dimer may be dissolved in the water of the fish-holding pond because it is believed that the active drug may also be resorbed via the gills of the fish. In case of bee-keeping, lysozyme dimer compositions can be applied by dissolving solid compositions in drinking water, tea, sugar solutions or other usual liquids prepared for the bees, e.g. as a feed substitute. It might, however, also be prepared as a—preferably concentrated—aqueous solution and mixed with honey, in order to ensure uptake of the drug by the bees.

A composition for oral use may, however, also be in the form of an osmotic system. Where appropriate, the local application of antiseptic dressings or tampons impregnated with an effective dose of the highly purified lysozyme dimer can be useful and beneficial.

The various types of the above mentioned lysozyme dimer compositions are preferably administered in a single or repeatable dose of about 0.001 to 0.5 mg/kg of body weight, especially at a dose of about 0.01 to 0.1 mg/kg of body weight. It goes without saying that the required concentration of active lysozyme dimer in the final pharmaceutical composition depends primarily on the size of the human or animal patient and of the kind of therapy or prophylactic treatment scheduled for the concerned patient. In most cases, however, the above mentioned concentration ranges are sufficient for a proper treatment. Nevertheless, it might become necessary, particularly in veterinary medicine, to increase the actual lysozyme dimer concentrations in the composition to a value beyond the 10 mg/ml and below the solubility product of the dimer in the respective solvent, i.e. to about 20 mg/ml of liquid or ointment. In doing so, the volume of the composition to be administered can be kept to a reasonable minimum for the ease of handling.

If possible, a combined administration protocol of the aforementioned compositions is preferred over a single therapy of either oral, parenteral or topical application.

Due to the essentially untoxic character of the highly purified lysozyme dimer, the compositions containing such dimer may be administered over a long period of time, i.e., months or even years, without causing harmful side effects. The time intervals for prophylactic or therapeutic administration of the drug may typically range from one or more times daily to weekly and monthly dosages and may also comprise even longer intervals, depending on the respective patient and the urgency of treatment as well as on the efficacy of the immunostimulation by the lysozyme dimer.

As indicated above, the present invention was at least partly made possible through the availability of high grade lysozyme dimer. The striking difference of product quality and, in particular, of the undesired lysozyme monomer share, is demonstrated by FIG. 1:

Lane 1 represents LMW prestained protein standards: Phosphorylase B 142.000 dalton, BSA 97.000, ovalbumin 50.000, carbonic anhydrase 35.100, soybean trypsin inhibitor 29.700, lysozyme 21.900 (Biorad, USA);

lanes 2 and 3 show purified lysozyme dimer LYDIUM KLP®602 (KLP-602 available from Nika Health Products), lot 506449, laboratory control; lane 2 loaded with 6.6 μg and lane 3 with 19.8 μg;

lanes 4 and 5 show another batch of KLP-602, lane 4 loaded with 6.6 μg and lane 5 with 19.8 μg;

lanes 6 and 7 show a lysozyme dimer preparation (KIW-607) manufactured according to Sorrentino et al., Eur. J. Bioch. 124, 183–189 (1982); lane 6 loaded with 6.6 μg and lane 7 with 19.8 μg.

The purified lysozyme dimer preparation KLP-602 contains four times more dimer than the compared product KIW-607, whereas the compared product KIW-607 contains six times more monomer than KLP-602.

In order that the invention described herein may be more fully understood, the following examples are set forth. It should be understood that these examples are for illustrative purposes only and are not to be construed as limiting this invention in any respect.

EXAMPLE 1

Lysozyme Dimer (XLP-602) in the Treatment of Lymphatic Leukemia in AKR Mice.

Materials and Methods

Seven months old mice of both sexes of leukemic strain AKR, inoculated with Graffi virus from the Inbreeding Animal Center, Institute of Immunology and Experimental Therapy, Polish Academy of Sciences, Wroclaw, were used in the study. In AKR mice early activation of endogenous leukemic virus takes place, which leads to clinical manifestations of lymphatic leukemia at the age of seven to nine months. The mice were divided into three groups of 30 animals each:

Group I (experimental)
  animals were given KLP-602 subcutaneously once at a dose of 20 µg/kg in 0.3 cm3 PBS;

Group II (experimental)
  animals received KLP-602 twice, at the same dose as above;

Group III (control)
  animals received 0.3 cm³ PBS twice.

The mice were killed by bleeding three and six weeks after the last KLP-602 injection (10 mice from each group). Ten mice from each group were left alive.

The Following Examinations were Performed

1. Measurement of the total body weight and the mass of the internal organs such as liver, spleen, thymus and external cervical lymph nodes, with the estimation of the organ mass to total body weight ratio. The therapeutic activity ratio was evaluated using the formula L/K×100%, where L is the mean survival time of the mice treated with KLP-602 and K is the mean survival time of the controls.

2. Histopathological examinations of the biopsies of the liver, spleen, thymus and lymph nodes. Sections were stained with H+E of the Gomori method for reticular fibers.

3. The level of free radicals in the serum was estimated using the chemiluminescence (Chl) method which allows detection of very weak photon luminescence of the serum.

4. Phagocytic activity of the polymorphonuclears (PMN) was estimated using NBT and chemiluminescence (Chl) tests.

Results

Single (Group I) and double (Group II) subcutaneous administration of KLP-602 to the highly leukemic AKR mouse strain, at a dose of 20 µg/kg, caused a statistically insignificant increase of body weight, and a decrease of the mass of internal organs such as: spleen, thymus, lymph nodes and liver (the last one was statistically insignificant) in comparison with the control animals (Group III) measured after three weeks of study (Table 1).

Increase of total body weight in both treated groups, decrease of the mass of the spleen, thymus and lymph nodes in Group I, and the increase of liver and thymus in Group II, when compared with the controls (Group III) occurred after six weeks of the study (Table 1).

Table 2 shows the ratio of the internal organs' weight to the total body weight. After three weeks the increase of thymus mass was observed in Group III (control) in comparison with both experimental groups (I and II). After six weeks, there was an increase of the mass of the spleen, thymus and lymph nodes in Groups II and III when compared with Group I.

The histopathological examinations conducted after three and six weeks revealed moderate (in the experimental groups) and excessive (in the control group) colonization of the cervical lymph nodes, thymus and spleen with lymphoid cells. However, the leukemic infiltrates in the liver were found only in the control. The lymphoid cells had oval or circular hyperchromatic nuclei with numerous nucleoli and atypical mitotic figures. These cells were accompanied by scanty low-differentiated centroblastic cells, reticulum cells and isles of proliferating megakaryocyes in the spleen. This stroma of the lymphatic organs such as the spleen, lymph nodes, and thymus contained scanty, thin reticulum fibers.

Chemiluminescence Examinations

The activity of free radicals in the sera of the control mice was $K=18\times10^{-3}$ after three weeks of the study. In Group II the activity of free radicals was lower ($K=10\times10^{-3}$). After six weeks the free radicals level was $K=10\times10^{-3}$ in the control animals, lower in Group II ($K=16\times10^{-3}$), and slightly higher in Group I ($K=1.5\times10^{-3}$). The marked increase of the phagocytic activity of PMN was noted in both experimental groups as compared with the control group after three weeks and was: 4688 Ch1 (Group I), 3485 Ch1 (Group II), and only 2052 Ch1 for the control Group. After six weeks the phagocytic activity in Group II was equally high (3264 Ch1) and it was lower in Group I (2477 Ch1). A significant increase of phagocytic activity measured by a NBT test was noted after three weeks in both treated groups and was 0.27 and 0.26 in Groups I and II, respectively. After six weeks increase of phagocytic activity was lower and took place only in Group II. Phagocytic activity in the control group was 0.22.

The therapeutic efficacy index of KLP-602 was 128% and 150% in Groups I and II respectively, being above the minimal 125%. This indicates the marked immunostimulative properties of KLP-602 and qualifies it for further studies.

The leukemic infiltrates were considerably smaller in both experimental groups than in the control group and were even absent in some mice. The leukemic infiltrates were present in the thymus, spleen and lymph nodes. In addition, they were found in the liver of the control animals. The results of the study indicate that KLP-602 can partially inhibit or delay the progress of leukemia in AKR mice. To the contrary, the rapid enlargement of the lymphatic organs with morphological changes, typical for well differentiated lymphoid leukemia, occurred in the animals treated with the placebo.

Moreover, KLP-602 inhibits the increase of free oxygen radicals in mice serum. It inhibits free radical processes similar to the action of antioxidants such as vitamin E, C, or selenium. It is possible that the inhibition of the leukemic cell proliferation in AKR mice treated with KLP-602 depends on the inhibition of free radical induced processes. In control mice (without KLP-602) the level of free radicals was higher and correlated with the intensity of the disease.

KLP-602 also stimulates the phagocytic activity of the mononuclear phagocyte system (MPS) measured by two independent methods, NST and Ch1, and thus stimulates cell-mediated immunity. It can also modulate TNF synthesis. Moreover, the "tumor rejection antigens" present on the leukemic cell surface can be recognized by T-cells cooperating with MPS. The tumor anti-infiltrating lymphocytes (TTL), 50–100% more effective than lymphokine-activated killers (LAK), are among those T-cells. They have $CD^4$ Or $CD^8$ or mixed phenotype and they express the IL-2 receptor on their surface. It is still unknown why they are paralyzed by neoplastic cells.

The reticulo-endothelial system with MPS cell stimulation is an essential immunological and antiviral mechanism. Stimulation of these cells results in interferon production and indirectly activates specific and non-specific immunological processes, B-cell, T-cell or NK dependent.

The MPS cells participate in immunological processes through their receptors such as Fc receptors, $C_3$ receptors or class II HLA receptors and also lectins, transferring, urokinase, insulin and fifty other lesser-known receptors. Any changes of their expression and affinity indicate activation of the cells. MPS cells can phagocytize NO-sensitive cells because they can synthesise this substance. The activated phagocytes are called "angry macrophages" or "blood thirsty" cells. MPS cells can destroy viruses through their cytotoxic and cytolytic properties, defective virion production and interferon synthesis.

The promising results of the preliminary study on AKR mice indicate that KLP-602 can successfully be used in the treatment of leukemia in AKR mice.

TABLE 1

Total body mass (g) and mass of internal organs (mg) in control and experimental mice (x ± S; upper values indicate x, lower values indicate S)

| Group | Three Weeks | | | Six Weeks | | |
|---|---|---|---|---|---|---|
| | I | II | III | I | II | III |
| Total Body Mass | 25.27 | 26.20 | 23.96 | 26.77 | 27.30 | 25.57 |
| | 2.22 | 1.67 | 1.23 | 1.10 | 2.34 | 1.68 |
| Spleen | 0.07 | 0.08 | 0.09 | 0.07 | 0.23 | 0.22 |
| | 0.00 | 0.02 | 0.01 | 0.00 | 0.01 | 0.00 |
| Thymus | 0.06 | 0.07 | 0.08 | 0.08 | 0.21 | 0.15 |
| | 0.01 | 0.02 | 0.02 | 0.01 | 0.03 | 0.07 |
| Lymph Nodes | 0.04 | 0.04 | 0.05 | 0.04 | 0.07 | 0.08 |
| | 0.00 | 0.00 | 0.01 | 0.00 | 0.04 | 0.04 |
| Liver | 1.38 | 1.36 | 1.43 | 1.61 | 1.89 | 1.67 |
| | 0.15 | 0.38 | 0.05 | 0.18 | 0.42 | 0.15 |

TABLE 2

Internal organs' mass to total body mass ratio in control and experimental mice (%)

| Group | Three Weeks | | | Six Weeks | | |
|---|---|---|---|---|---|---|
| | I | II | III | I | II | III |
| Spleen | 0.30 | 0.31 | 0.37 | 0.29 | 0.84 | 0.87 |
| Thymus | 0.23 | 0.26 | 0.33 | 0.33 | 1.06 | 0.61 |
| Lymph Nodes | 0.18 | 0.18 | 0.21 | 0.15 | 0.26 | 0.26 |
| Liver | 5.49 | 5.25 | 5.81 | 6.02 | 6.35 | 6.40 |

EXAMPLE 2

Effect of a Highly Purified Lysozyme Dimer Preparation (KLP-602) on Hair Growth in Alopecia Areata.

The study was conducted to determine whether a balsam containing KLP-602 acts on hair growth in alopecia areata. In addition, the tolerability of this balsam when applied on the skin was estimated.

Materials and Methods

The study was a controlled, comparative clinical study. Twelve subjects (two male and ten female patients) with alopecia areata in "telogen" stage in general good health condition were involved in the study. They were aged from 19 to 50 years. Twelve subjects (three male and nine female patients) with alopecia areata treated with MINOXIDIL® (6-(1-piperidinyl)-2,4-pyrimidinediamine-3-oxide, or, in the alternative, 2,4-diamino-6-piperidinopyrimidine-3-oxide, hereinafter referred to as MINOXIDIL® were considered as a control group. Their ages ranged from 19 to 49 years. The distribution of subjects by sex and age within two treatment groups was similar for the two groups.

Patient Selection Criteria

Inclusion criteria:
1. Alopecia areata in "telogen" stage;
2. Age 18–50 years.

Exclusion criteria:
1. Alopecia areata in "dystrophy" stage;
2. Another type of alopecia;
3. Any other skin disease.

Concomitant Medication

Concomitant medication was not allowed unless it was required for treating the general health conditions.

Assignment of Treatment Numbers

During the study persons who fulfilled the selection criteria were numbered in tested groups in sequential order. The investigator entered the corresponding number in the appropriate place on each Case Report Form (CRF).

Trial Medication

The hair balsam manufactured by NIKA according to the original formula was provided in 100 ml identical plastic bottles with a calibrated small-tipped dropper. A 0–05% KLP-602 lotion was applied on the scalp three times a day according to the instructions of the attending dermatologist. The treatment began immediately after recognizing alopecia areata by the dermatologist.

A 2% MINOXIDIL® solution was applied twice daily to affected skin areas.

The duration of the treatment was 16 weeks. After the treatment the patients were observed for 2 months of the follow up period.

Evaluation of Safety

Subjects for both tested groups were screened by means of a full history and medical examination for entry and end of study. Blood and urine samples for routine laboratory test were taken before and after treatment. Laboratory studies included the following tests:

Hematology

Hemoglobin, hematocrit, total and differential white cell count

Serum Biochemistry

ALT (GPT), AST (GOT), alkaline phosphatase, bilirubin

Urine dipstick urine analysis for protein, blood and glucose.

Patients were seen monthly during 4 months of therapy and 2 months of follow up period. At each visit, the subjects were questioned about the presence of general or local adverse events such as irritation, burning, itching; treatment areas were examined for erythema or other local side effects.

Evaluation of Efficacy

Efficacy parameters
1. The primary efficacy parameter was the hair growth
2. The secondary efficacy parameter was healing time of the altered scalp.
3. Photographic documentation was taken at the following points in the study:
   before application of hair balm with KLP-602
   at the time of hair growth
   at the end of application hair balm with KLP-602

Microscopic evaluation (trichogram) was performed. Standardized trichograms on hair taken from the border of alopecia areata lesions reveal most useful information on the course and severity of the disease and also efficacy of therapeutic measures.

At each visit, the scalp was evaluated for signs of hair growth which was categorized as:

none slight—visible regrowth (vellus or few scattered solitary terminal hairs)

moderate—incomplete (partial)

complete

"cosmetically acceptable" hair growth was defined as sufficient to cover the scalp and conceal areas of residual hair loss.

Results

All the subjects enrolled to the study (12 treated with 0.05% KLP-602 and 12 from control group treated with 2% MINOXIDIL® solution) completed a 4 months therapy period and 2 months follow up.

Efficacy

The most useful measure of efficacy was the investigators' assessments at the end of the study. Overall, eight of the twelve subjects (66%) in KLP-602 group and six of twelve subjects (50%) in the MINOXIDIL® group showed increased hair growth during the study. Of these, four subjects in the KLP-602 group (33%) and three in the MINOXIDIL® group (25%) were considered to have complete, cosmetically acceptable hair growth. Partial hair growth was seen in three from twelve assessable subjects in the KLP-602 group (25%) and three in the MINOXIDIL® group respectively (25%). In one subject in the KLP-602 group (9%) minimum hair growth was observed. There was no hair growth in four of twelve (33%) in the KLP-602 group and in six of twelve (50%) in the MINOXIDIL® group.

In the KLP-602 group with alopecia at an extent of less than 25% of the scalp, hair growth was obtained in eight out of eight subjects and in six out of seven in the MINOXIDIL® group, respectively. No regrowth was observed in subjects with alopecia at an extent of more than 25% of the scalp in both treated groups.

The mean time of hair growth response in correlation with the duration of the treatment ranged from one until three months in both groups. Three subjects in the KLP-602 group responded after one month of treatment. In one female the hair growth after one month was with terminal hair of about 5 mm length and the bald scalp areas were covered with dense hair regrowth.

At the control visit after the second month this woman appeared with alopecia totalis (emotional stress—divorce) and she did not respond to the further treatment, completed the study with negative result. In one subject in the MINOXIDIL® group hair regrowth was observed after one month of therapy. In four patients in the KLP-602 group hair regrowth was obtained after two months of treatment. After three months of the study hair regrowth was observed in two subjects in the KLP-602 group and in three of the MINOXIDIL® group, respectively.

Safety

No general side effects were observed during the therapy and follow up period. No abnormalities in laboratory blood and urine values were noted at the baseline and at the end of the study in both treated groups.

Local adverse events observed during the study: One female in the KLP-602 group complained of burning and itching of the scalp in the second month of the treatment. She connected these symptoms with wearing of a new wig. The sensations disappeared within two weeks without any additional treatment, she did not stop the therapy and completed the study with good result. One subject treated with 2% MINOXIDIL® solution complained of greasy hair, no significant clinical signs were observed in the examination of the scalp. The patient correlated this event with the trial but he was willing to continue the treatment.

No significant findings were noted in correlation of the hair regrowth and the age of patients, localization of bald areas and the duration of the current episode, which was short and similar for both groups and rated from one week to one year maximum. All non-responders in both treated groups had alopecia areata anamnesis lasting for at least five years (5–15 years).

Discussion

The study was to evaluate the safety and efficacy of topically applied 0–05% KLP-602 lotion the hair growth in patients with alopecia areata and to compare it with the effectiveness of a 2% MINOXIDIL® solution during a four months therapy.

The hair balsam containing KLP-602 was well tolerated by patients. 66% of subject treated with 0–05% KLP-602 lotion showed the increased hair growth during the study in comparison to 50% of subjects in MINOXIDIL® group.

Cosmetically acceptable hair growth was seen in 33% of patients in KLP-602 group and in 25% in MINOXIDIL® group respectively. Better treatment results were observed in patients with an extent of alopecia lower than 25% of the altered scalp. 0.05% KLP-602 lotion was easy to use topically and did not cause any local nor general adverse events. Considering the short time of the study (16 weeks) the results obtained are very encouraging.

Conclusions

1. The hair balm containing KLP-602 was well tolerated and did not cause any side effects.
2. Topical application of 0–05% KLP-602 was easy and safe.
3. No local or general side effects and no derives in laboratory values were observed during the study.
4. Due to short time of the therapy (4 months) and 2 months follow up, the complete assessment of the results and performance of the treatment was impossible, although this period was long enough to observe encouraging efficacy of treatment.
5. The results obtained in the trial showed that 0.05% KLP-602 lotion is comparable to a 2% MINOXIDIL® solution and even more effective in alopecia areata treatment.
6. Preclinical investigations and the results obtained in the study demonstrate that KLP-602 applied topically induces hair growth with patients suffering from alopecia areata.

Summary

The study was performed to estimate efficacy and tolerability of a hair balsam containing KLP-602 on hair growth in alopecia areata. Applications of 0.05% KLP-602 lotion three times a day were generally well tolerated in the 4 months treatment period. No local or systemic side effects were observed. Better hair growth response was seen in the KLP-602 group than in the MINOXIDIL® group. Hair regrowth response was observed in 66% of the subjects with 0.05% KLP-602 lotion. The percentage of patients who responded with moderate or dense hair regrowth was greater among the patients whose balding area involved less than 25% of the scalp. 0.05% KLP-602 seems to be a remarkable agent in alopecia areata treatment.

EXAMPLE 3

Prophylactic Application of Lysozyme Dimer to Induce a Non-specific Stimulation of the Immune System of Fish Test Design Three hundred healthy fish of the species rainbow trout (*Oncorhynchus mykiss*, family of salmonidae), weighing 90–100 g each, were subjected to the trial. Lysozyme dimer manufactured according to WO91/10731 (herein designated "KLP-602") containing about 10% by weight or less of unintended by-products and being essentially free from the monomeric form of lysozyme was dissolved in PBS to prepare injection solutions for the administration of 10 and 100 µg lysozyme dimer per kg body weight, suitable for intraperitoneal injection into fish. The drug was administered once a day. The therapeutical protocol comprised different groups of fish subjected to drug application either on day 1 only, on day 1 and day 3, or on days 1, 3 and 5, respectively. The fish of the control group were not subjected to lysozyme dimer administration.

After 1, 2, 3 and 4 weeks from the administration of the last injection 10 individuals each were sampled from each of the treated groups, and from the control. The fish were immobilized and about 2 ml blood were collected from the caudal vein by means of a heparinized vacuette (Greiner). The phagocytic ability of PMN and MN cells, the respiratory burst activity and potential killing activity of PMN and MN cells, the MPO activity in PMN phagocytes, and lysozyme and gammaglobulin levels in the serum were determined.

Also, 20 individuals of each group were subjected to a disease (furunculosis) challenge test. The fish were given single intraperitoneal injections of a bacterial suspension of *Aeromonas salmonicida* grown on nutrient broth for 48 hours. The mortality (death rate) of the animals was determined and its interrelationship with the applied bacterial infection was confirmed by the isolation of pathogens from the kidneys of dead animals.

Results

In the KLP-602 treated groups, all of the above mentioned immunological parameters were significantly increased ($P<0.05$) over the corresponding values of the control group. This surprising result was observed in all groups, i.e., after one-, two-, or threefold application of KLP-602 and lasted for the entire observation period of up to 4 weeks after the last injection.

Also, the mortality of fish in the KLP-602 treated groups was significantly lower than in the control group. Respiratory burst activity was even considerably higher, as were the phagocytic indexes and neutrophil myeloperoxidase (MPO) levels of the groups treated by two- and threefold application of KLP-602.

The known susceptibility of rainbow trout to virulent bacterial challenge by *A.salmonicida* and the results observed with the groups prophylactically treated with the lysozyme dimer composition suggest that the drug in fact was able to induce a short-term protection against said microbial challenge. It was further recognized, that the protection was higher in the groups that received two or three doses of KLP-602 than in the groups treated by a single application only.

Conclusion

The application of highly purified lysozyme dimer to fish enhances the non-specific defense mechanisms and significantly improves the protection against microbial challenge, e.g., by *A.salmonicida* (causing furunculosis). This observation is of a great importance for a prophylactic and therapeutic treatment of fish in the fish breeding industry in order to minimize the losses of fish due to frequently occurring fish diseases, particularly during the spring season.

EXAMPLE 4

Therapeutic Application of Lysozyme Dimer to Induce a Non-specific Stimulation of the Immune System of Fish Test Design Two hundred rainbow trouts were involved in this comparative study of non-specific defense mechanisms in the course of a naturally occurring infection with IPNV (Infectious Pancreatic Necrosis Virus) and upon application of a composition comprising dimerized lysozyme (KLP-602). After the identification of IPNV infection, part of the fish were treated with KLP-602, while a control group remained untreated. The major parameters characterizing the non-specific cellular and humoral defense mechanisms were analyzed by immunological and serological methods. These methods included the weekly determination of the total leukocyte number, relative leukocyte count, phagocytic ability of PMN and MN cells, respiratory burst activity and potential killing activity, MPO activity in neutrophils, lysozyme and ceruloplasmin activity in the plasma, and total protein and gamma-globulin levels, during an observation period of 2 months.

Replicated groups of rainbow trout were fed diets containing the non-specific immunostimulant KLP-602 at a dose of 20 µg per kg body weight. Lyophilized samples of KLP-602 were applied together with nutrients either orally in solid form (flocs, pellets) or dissolved in the water of the fish-holding pond, i.e., as an aqueous solution, for a period of seven days. It is assumed that the drug might also be resorbed by a pathway via the gills of the fish.

Thereafter, they were sampled and assayed for changes in non-specific cellular and humoral defense mechanisms in weekly intervals. Each time, 10 fish were randomly selected for the immunological assays and the identification of IPNV. In addition, all fish were observed daily for unusual behaviour, morphological changes and mortality.

Results

In fish naturally infected by IPNV an immunosuppressive effect could be observed. Throughout the entire observation time the parameters indicating the non-specific cellular and humoral defense mechanisms were significantly reduced, whereas one week after feeding the lysozyme dimer containing diet some parameters, e.g., ceruloplasmin level, respiratory burst activity, immunoglobulin level, and lysozyme activity were significantly increased (e.g., approx. 31% increase of ceruloplasmin level; approx. 40% increase of lysozyme activity; approx. 33% increase of respiratory burst activity) when compared to the control group. After application of KLP-602 immunostimulating effects on the non-specific defense mechanisms were unambiguously identified. Also, the cumulative mortality was lowest in the groups fed with the KLP-602 containing diet.

Conclusion

Fish treated with a diet containing lysozyme dimer (KLP-602) showed advantageous changes of the non-specific immunological defense mechanisms. These changes correlated with reduced mortality, i.e., indicating protection against the naturally occurring infection by IPNV, which finding strongly recommends to further develop and optimize the strategy of prevention and/or therapy of fish diseases by administration of the lysozyme dimer as referred to herein.

EXAMPLE 5

Administration of Lysozyme Dimer to Assess Restoration of Humoral Response in Cyclophosphamide-suppressed Mice Material and Methods Animals Male and female Balb/c mice, weighing 18–20 g and being of 8–10 weeks old were used as test subjects. The mice were delivered by a breeding center of Medical University, Wroclaw. The mice were immunized i. p. with 0.2 ml of 10% SRBC suspension ($4 \times 10^8$ erythrocytes per animal). The erythrocytes were obtained from sheep blood collected in a sterile manner and next kept in Alsever's solution for at least 3 days.

Reagents

The following reagents were used:
1) Lysozyme dimer (Lydium-KLP, available from Nika Health Products, Switzerland)

2) cyclophosphamide (Endoxan-Asta)
3) Ficoll 400-Pharmacia
4) meglumine diatrizoate with sodium diatrizoate (Uropolinum 75%—Polfa)
5) 2-mercaptoethanol (2-ME Sigma)
6) agarose—Serva
7) Hank's saline—Biomed
8) phosphate buffered saline (PBS) pH 7.2 0.15 M—Biomed
9) guinea pig complement—Biomed
10) Alsever's solution, prepared in our laboratory Immunosuppression Pharmacological immunosuppression was induced by a single i. p. injection of cyclophosphamide administered at a dose of 200 mg/kg, 6 days prior to SRBC immunization.

Experimental Protocol

Lysozyme dimer (Lydium-KLP, Nika Health Products) was injected i. p. according to the following different experimental protocols. Administration of lysozyme dimer to immunized cyclophosphamide-suppressed animals: (i) a single dose of 20 µg/kg at 2, 4 or 6 days prior to cyclophosphamide; (ii) two doses (20 µg/kg each) at 2 and 6 days prior to cyclophosphamide; (iii) three doses (2 µg/kg or 20 µg/kg each) injected at 48 hour intervals prior to cyclophosphamide or after its administration; and (iv) three doses (2 µg/kg or 20 µg/kg each), injected at 24 hour intervals following SRBC immunization.

Parallel studies were carried out in two control groups. One control group consisted of SRBC-immunized mice treated with cyclophosphamide at 6 days before SRBC. The mice in the other control group received phosphate buffered saline (PBS) instead of cyclophosphamide. The volume of each dose of lysozyme dimer, cyclophosphamide or PBS was 0.2 ml per mouse.

Plaque Forming Cells (PFC)

The mice were killed by cervical dislocation. The spleens were removed and placed in disposable Petri dishes containing sterile Hank's saline. The spleens were teased apart with forceps by gently tearing the capsule and releasing the cells. The suspended cells were centrifuged on a layer of Ficoll/Uropolinum 75% (density 1.071); the interface was collected and washed twice. After the second wash the cells were suspended in Hank's saline at a final concentration of $1 \times 10^6$ per ml.

The splenocytes producing anti-SRBC antibodies were determined by local haemolysis technique in gel according to Mishell and Dutton, "Immunization of Dissociated Spleen Cell Cultures from Normal Mice," *J. Exp. Med.,* 186, pp. 423–442. The measurements were carried out 4 and 7 days after immunization.

Anti-SRBC Antibodies in the Serum

The blood samples were taken from orbital socket of ether anaesthetized mice Serum was obtained by centrifugation of coagulated blood and inactivated at 56° C. for 30 min. The total and 2-mercaptoethanol resistant (MrH) serum agglutination titre were defined on days 4 and 7 following SRBC immunization using active haemagglutination test as described by Adler, "Studies on Mouse Antibodies. II. Mercaptoethanol-Sensitive 7S Antibodies in Mouse Antisera to Protein Antigens," *J. Immunol.,* 95, pp. 26–47, carried out in microplates. The titre of 2-mercaptoethanol resistant antibody is roughly equivalent to that due to IgG in the serum, and so the greater titre obtained without 2-mercaptoethanol was due to the IgM.

Statistical Analysis

The data obtained in the study were analyzed statistically using a t-test.

Results

Figure 2A:
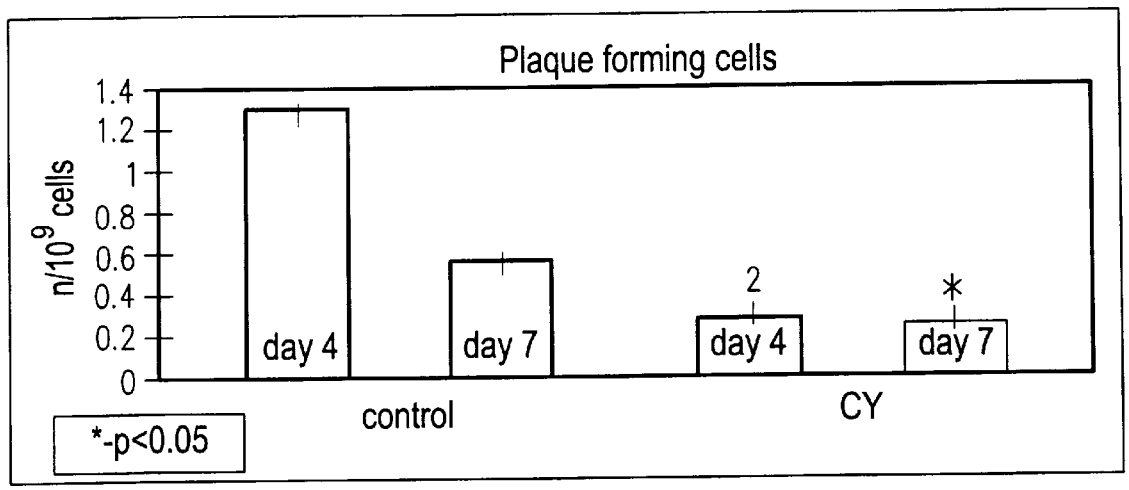
FIGS. 2A and 2B shows the effect of cyclophosphamide on humoral response of SRBC-immunized mice.
Figure 2B:
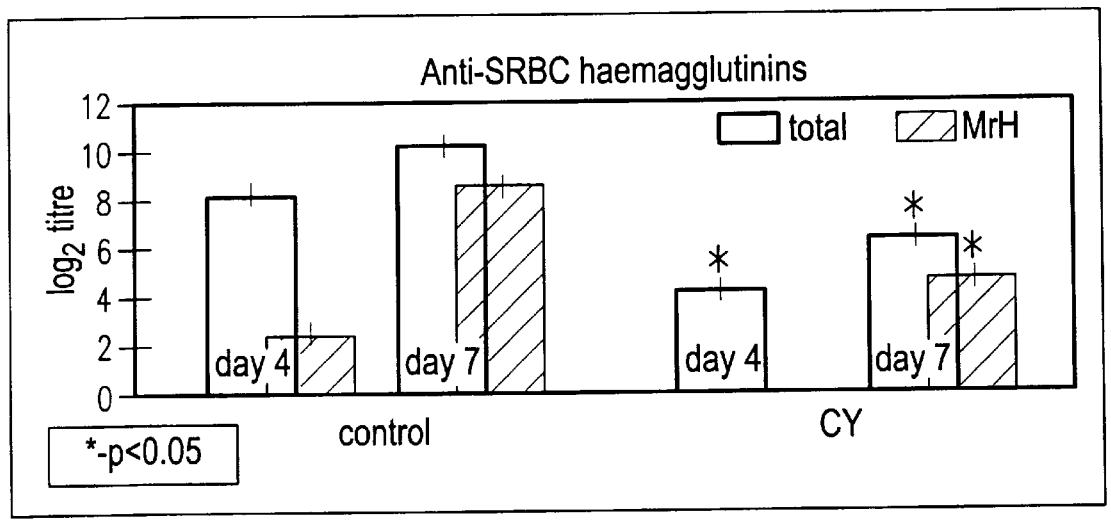

1. The effect of cyclophosphamide on humoral response of SRBC-immunized mice is shown in FIGS. 2A and 2B.

A single dose of cyclophosphamide (200 mg/kg) injected 6 days prior to SRBC markedly reduced humoral response to the antigen. Immunosuppression due to cyclophosphamide decreased the number of PFC and discontinued the production of total and MrH anti-SRBC haemagglutinins. The suppressive effect of cyclophosphamide was observed for 7 days.

2. A dose-dependent effect of lysozyme dimer administered prior to cyclophosphamide on humoral response of SRBC-immunized mice is shown in FIG. 3.

A single dose of lysozyme dimer (20 µg/kg) administered prior to immunosuppression, to some extent, prevented the suppressive action of cyclophosphamide, which consequently resulted in a slightly reduced number of PFC, observed 4 and 7 days after injection of the antigen. No effect of lysozyme dimer on total anti-SRBC haemagglutination titer was observed.

Lysozyme dimer (20 µg/kg) injected twice prior to immunosuppression not only resulted in lower reduction of PFC, but also in partially restored ability of the cells to produce haemagglutinins.

Lysozyme dimer (20 µg/kg) administered three times prior to cyclophosphamide proved to be the strongest protection against cyclophosphamide, resulting in partial increase in PFC (day 4) and restored ability of the cells to produce haemagglutinins. Three injections of lysozyme dimer at doses ten times as low (2 µg/kg), administered at 48 hour intervals, prior to cyclophosphamide, only partially inhibited the immunosuppressive action of the latter.

Figure 4A:
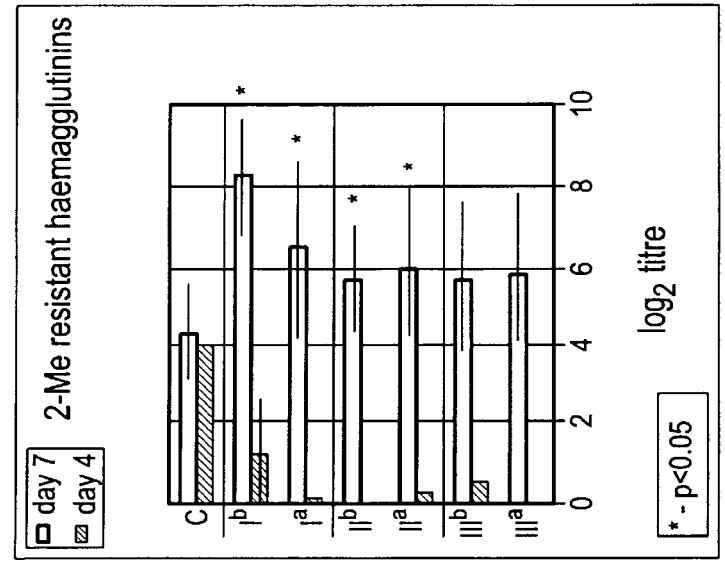
FIGS. 4A, 4B and 4C shows effect of lysozyme dimer on humoral response in cyclophosphamide-treated mice depending on the time of exposure to the drug in relation to SRBC.
Figure 4B:
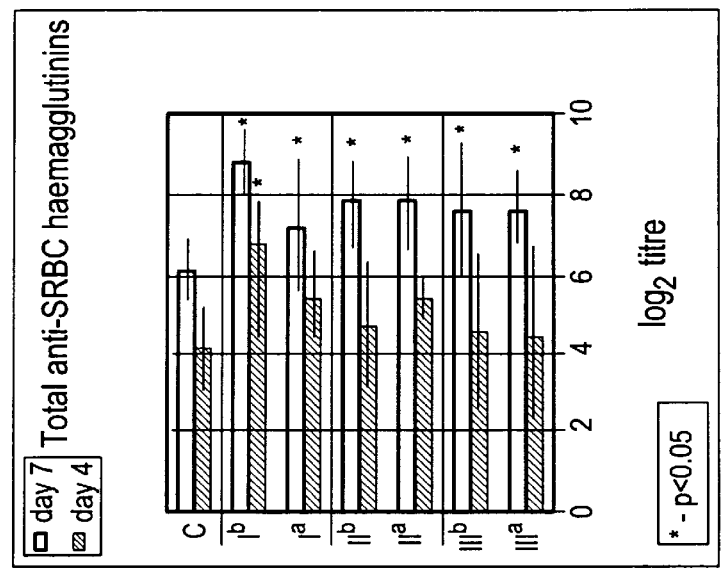
Figure 4C:
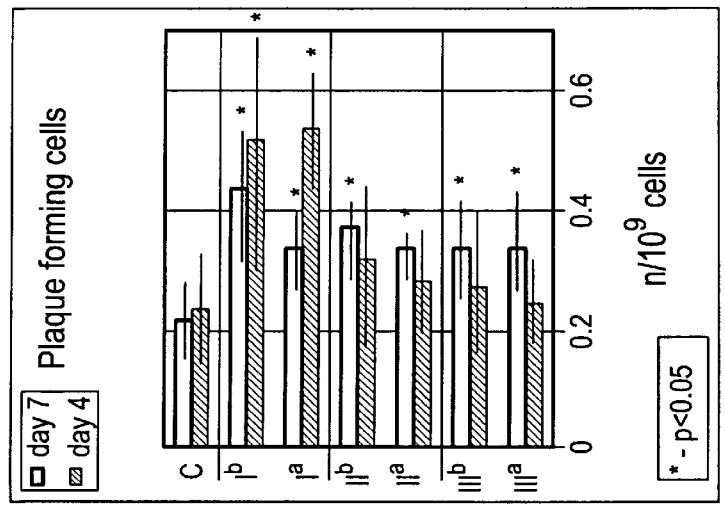

3. The effect of lysozyme dimer on humoral response in cyclophosphamide-treated mice depending on the time of exposure to the drug in relation to SRBC is shown in FIGS. 4A, 4B and 4C.

Lysozyme dimer (2 µg/kg or 20 µg/kg) administered three times at 48 hour intervals after cyclophosphamide did not affect the suppressive action observed 4 days after cyclophosphamide administration. In contrast, 7 days after SRBC immunization, lysozyme dimer inhibited the suppressive action of cyclophosphamide and resulted in lower reductions in PFC and MrH titer.

Lysozyme dimer (2 µg/kg or 20 µg/kg) administered three times at 24 hour intervals after SRBC immunization did not reduce the suppressive action of cyclophosphamide observed 4 days after its administration, but after 7 days the number of PFC and antibody titers increased.

Discussion

This Example shows that humoral response of SRBC-immunized mice, reduced by high cyclophosphamide dose (200 mg/kg) can be protected successively by lysozyme dimer. The studies on the effect of cyclophosphamide on primary humoral response show that the suppression action of this drug depends primarily on the time of its administration in relation to the antigen, and also on cyclophosphamide and antigen doses. See, Aisenberg, "Studies on Cyclophosphamide Induced Tolerance to Sheep Erythrocytes," *J. Exp. Med.,* 125, pp. 833–837, and Askenase et al., "Augmentation of Delayed Type Hypersensitivty By Doses of Cyclophosphamide Which Do Not Affect Antibody Responses," *J. Exp. Med.,* 141, pp. 697–702. Reduction in primary humoral response of cyclophosphamide-treated animals to T-dependent and T-independent antigens occurs 2 to 6 days after antigen stimulation. See, Braun and Harris, "Modulation of the Immune Response By Chemotherapy," *Pharmac. Ther.,* 14, pp. 89–122. The immunosuppressive effect of cyclophosphamide is primarily reflected in the restoration of B lymphocytes (which lasts over 21 days after cyclophosphamide administration), and T-suppressor and T-helper lymphocytes, which exhibit restored activities between day 5 and 11 after a single injection of high cyclophosphamide dose. See, Braun and Harris, supra, and Willers and Sluis, "The Influence of Cyclophosphamide on Antibody Formation in the Mouse," Ann. Immunol., 126C, pp. 267–279. Recent studies have shown that a single injection of cyclophosphamide at a dose as high as 200 mg/kg induces heterogeneity of splenic suppressor (NS) cells in mice. Nikcavich et al., "Stimulation of Suppressor Cells in the Bone Marrow and Spleens of High Dose Cyclophosphamide-Treated C57BL/6 Mice," Cell Immunol., 109, pp. 349–359. The NS cells, whose suppressive activity is the strongest between day 5 and 11 after cyclophosphamide administration, are likely to decrease humoral response. Segre et al., "Cyclophosphamide-Induced Suppressor Cells in Mice: Suppression of the Antibody Response In Vitro and Characterization of the Effector Cells," Cell Immunol., 91, pp. 443–454. The studies at Brooks-Kaiser et al., "Heterogeneity of Splenic Natural Suppressor Cells Induced in Mice by Treatment With Cyclophsphamide," Immunopharmacol., 25, pp. 117–129, show that suppressive activity of cyclophosphamide-induced NS cells is connected with the production of soluble suppressor factors.

The data obtained in the present Example show that the lysozyme dimer affects the inhibiting action of cyclophosphamide on humoral response of SRBC-immunized mice and the effect depends on the dose and time of the drug administration in relation to cyclophosphamide. The strongest protection was observed after three doses of 20 $\mu$g/kg administered prior to pharmacological immunosuppression. Reduction in the dose to 2 $\mu$g/kg and shorter treatment resulted in reduced protective effects. It was found that the effect of three injections of either of the doses, between cyclophosphamide and antigen injection, or after antigen stimulation, was weaker and delayed as compared to that observed when the drug was administered prior to immunosuppression.

In conclusion, lysozyme dimer administered to mice before cyclophosphamide immunosuppression protects primary humoral response of mice effectively; the number of PFC and the level of anti-SRBC haemagglutinins increase. The protective action of lysozyme dimer is stronger when the doses as high as 20 $\mu$g/kg are administered several times, which suggests that this agent can be used successively to retard the degradation of the immune system by alkylating cytostatic agents.

The entire disclosure of each of the references discussed above in this Example is hereby incorporated herein by reference.

EXAMPLE 6

The Effect of Lysozyme Dimer on Selected Immunity Indicators in Sows Before Farrowing Perinatal disorders in sows, referred to as the CM syndrome (Coliform Mastitis), are characterized by such clinical symptoms as endometritis, mastitis, and agalactia, and they present significant health and economic problems in large-herd swine breeding. It is believed that the disorders are caused, among others, by immunosuppression that occurs in sows after farrowing. According to Garbulinski (1992), immune homeostasis can be protected against suppressive effects of environmental aggression factors with immunostimulants.

Over the last several years, agents capable of stimulating various immune mechanisms have been incorporated into the traditional therapy of some postpartum diseases in sows. Lydium-KLP has such properties. It is an immunotropic medication and it has stimulating properties. The active ingredient is lysozyme dimer (muramidase) whose chemical purity is higher than 98%. Lydium-KLP stimulates phagocytic processes, enhances alpha-interferon production by lymphocytes, inhibits production of TNF-beta, and shows synergism with antibiotics.

The purpose of this Example was to analyze the activity of selected indices of the immune system during the perinatal period in sows that received Lydium-KLP before farrowing. Included in the study were 60 pregnant clinically healthy sows randomly selected from a group of 320. The sows were fed full-portion diets according to broadly accepted nutritional principles. Farrowing was held in specially designated rooms in individual pens. 40 sows from the experimental group received Lydium-KLP one i.m. in a dose of 0.02 mg/kg of body weight 10 days before parturition. The control sows did not receive the preparation. Blood for immunological tests was collected before the preparation was administered and on day 10 after parturition. The following tests were used to assay cellular immunity indicators: the Angus and Yang blast transformation stimulated by phytohemaglutinin mitogen (LF-7), the Roman and Poland nitroblue tetrazolium reduction test (NBT), the Mueller esterase test, the Wright phagocytic test as modified by Dolezal including the Hamburger number, and the Wright and Davies index. Humoral immunity analysis included assays of total protein and its fractions in serum according to the biuret method and the electrophoretic separation method.

Mean values of the immunity indicators in sows before the immunomodulator was administered on day 10 before farrowing were within the range of values obtained in previous experiments and differences in values obtained for individual animals were statistically insignificant.

Decreased phagocytic activity of leukocytes, decreased activity of neutrophilic granulocytes and those transforming under LF-7 stimulation, and decreased gamma-globulin activity were observed in the control sows after parturition. This finding indicates that the sow's body enters and immunological niche after parturition.

Unlike the control animals, the experimental sows had a 65.2% higher phagocytic activity expressed by the Hamburger number, the Wright indicator was 44% higher, and neutrophil activity (NBT+) was 37.2 higher. In comparison with the control group, there was a statistically significant $p<0.01$ increase in the percentages of esterase-positive lymphocytes and those transforming under LF-7 stimulation (by 11.0 and 82% respectively). A statistically significant $p<0.01$ increase in the level of total protein, albumins, and alpha-, beta- and gamma-globulins was also observed. The gamma-globulin increase was particularly large. Within the leukogram, favorable quantitative changes occurred in the neutrophil fraction (a 17.8% increase) and in eosinophilic granulocytes (21.2%). The immunological condition of the sows during the perinatal period was reflected in the intensification of disorder in individual groups after farrowing.

What is claimed is:

1. A method for prophylactic or therapeutic intervention for a disease or condition caused by or associated with an immunological disorder, wherein the disease or condition is responsive to lysozyme dimer activity and is selected from the group consisting of a hair growth disorder being alopecia, and an infectious pancreatic necrosis virus (IPNV) infection in fish, comprising administering to a human or animal recipient in need thereof or benefiting therefrom a single or repeated dose of a pharmaceutical composition comprising lysozyme dimer in an amount effective for said prophylactic or therapeutic intervention.

2. The method according to claim 1, wherein said disease or condition is alopecia areata and said pharmaceutical composition is topically applied.

3. The method according to claim 1, wherein said disease or condition is IPNV infection in fish and the pharmaceutical composition is administered in solid form.

4. The method according to claim 1, wherein said prophylactic intervention comprises increasing phagocytic activity and at least one parameter selected from the group consisting of ceruloplasmin level, respiratory burst activity, immunoglobulin level, and lysozyme activity.

5. The method according to claim 1, wherein said lysozyme dimer contains about 10% by weight or less of unintended byproducts.

6. The method according to claim 1, wherein said composition is administered in a single or repeated dose of from about 0.001 to 0.5 mg/kg of body weight.

7. The method according to claim 6, wherein said dose is about 0.01 to 0.1 mg/kg of body weight.

8. The method according to claim 1, wherein said pharmaceutical composition is in a form of a gel, an ointment or a liquid composition and comprises the lysozyme dimer in an amount of from 0.01 to 10 mg/ml together with at least one additive selected from the group consisting of a physiologically acceptable solvent, a carrier, and a suitable preservative.

9. The method according to claim 1, wherein said pharmaceutical composition is in a solid form suitable for oral administration and comprises the lysozyme dimer in an amount of from 0.01 to 10 mg/g together with at least one physiologically acceptable additive selected from the group consisting of a carrier, a preservative, a flavor and a colorant.

10. A method for the treatment of alopecia areata comprising topically administering to the scalp of an afflicted recipient a repeated dose of a liquid composition comprising 0.05% of lysozyme dimer to initiate regrowth of hair at the treated area of the scalp.

11. The method of claim 10, wherein the composition is administered three times a day.

* * * * *